US008199994B2

(12) United States Patent
Amir

(10) Patent No.: US 8,199,994 B2
(45) Date of Patent: Jun. 12, 2012

(54) AUTOMATIC ANALYSIS OF CARDIAC M-MODE VIEWS

(75) Inventor: Arnon Amir, Saratoga, CA (US)

(73) Assignee: International Business Machines Corporation, Armonk, NY (US)

( * ) Notice: Subject to any disclaimer, the term of this patent is extended or adjusted under 35 U.S.C. 154(b) by 591 days.

(21) Appl. No.: 12/403,747

(22) Filed: Mar. 13, 2009

(65) Prior Publication Data
US 2010/0232665 A1 Sep. 16, 2010

(51) Int. Cl.
G06K 9/00 (2006.01)
(52) U.S. Cl. ............... 382/131; 382/132; 378/4; 378/8
(58) Field of Classification Search ............... 382/131; 378/8; 600/407, 437
See application file for complete search history.

(56) References Cited

U.S. PATENT DOCUMENTS

| 4,936,311 | A | | 6/1990 | Oe |
| 5,515,856 | A | | 5/1996 | Olstad et al. |
| 5,570,430 | A | * | 10/1996 | Sheehan et al. ............ 382/128 |
| 6,416,477 | B1 | * | 7/2002 | Jago ............ 600/447 |
| 6,447,450 | B1 | * | 9/2002 | Olstad ............ 600/437 |
| 6,514,207 | B2 | | 2/2003 | Ebadollahi et al. |
| 6,661,873 | B2 | * | 12/2003 | Jabri et al. ............ 378/98.11 |
| 6,683,972 | B1 | * | 1/2004 | Mathiak ............ 382/131 |
| 6,708,055 | B2 | | 3/2004 | Geiser et al. |
| 6,755,787 | B2 | | 6/2004 | Hossack et al. |
| 7,109,989 | B2 | * | 9/2006 | Bissell et al. ............ 345/424 |
| 7,668,358 | B2 | * | 2/2010 | Snoeren et al. ............ 382/131 |
| 7,912,259 | B2 | * | 3/2011 | Arditi et al. ............ 382/128 |
| 2003/0153823 | A1 | * | 8/2003 | Geiser et al. ............ 600/407 |
| 2005/0074153 | A1 | * | 4/2005 | Pedrizzetti et al. ............ 382/128 |
| 2005/0096543 | A1 | | 5/2005 | Jackson et al. |
| 2005/0119553 | A1 | * | 6/2005 | Pedrizzetti et al. ............ 600/410 |
| 2006/0034538 | A1 | | 2/2006 | Potter et al. |

OTHER PUBLICATIONS

Griffiths, Clive et al., "Computer Assisted M-mode Echocardiogram Analysis,"Clin. Phys. Physiol. Meas., 1982, V3, N2, pp. 103-114.
Lee, SH et al., "Using Synthetic M-mode Imaging to Measure Temporal Differences in Left Ventricular Contraction Patterns during Ischemia," Computers in Cardiology, Sep. 1997, V24, pp. 235-238.
Malpica, N et al., "A Snake Model for Anatomic M-mode Tracking in Echocardiography," Proceedings of the 3rd Int'l Symposium on Image and Signal Processing and Analysis, Sep. 2003, V2, pp. 722-726.
Teichholz et al., "Problems in Echocardiographic Volume Determinations: Echocardiographic-Angiographic Correlations in the Presence or Absence of Asynergy," The American Journal of Cardiology, V37, N1, Jan. 1, 1976, pp. 7-11.
Pelle et al., "Microcomputer-Based System for Automatic Analysis of M-mode Echocardiograms," Journal of Biomedical Engineering, V15, N4, Jul. 1, 1993, pp. 274-278.

* cited by examiner

Primary Examiner — Alexander H Taningco
(74) Attorney, Agent, or Firm — IP Authority, LLC; Ramraj Soundararajan; Geoff Trotter

(57) ABSTRACT

Automated analysis of M-Mode images are provided based on the separation of M-Mode images into tissue layers and motion curves by simultaneously aligning all layers and extracting the motion curves from the alignment. Also provided is the ability to search for similar M-Modes using a representation comprised of tissue layers and motion curves and a similarity measure thereof.

10 Claims, 12 Drawing Sheets

AUTOMATIC ANALYSIS OF CARDIAC M-MODE VIEWS

BACKGROUND OF THE INVENTION

1. Field of Invention

The present invention relates generally to the field of image analysis. More specifically, the present invention is related to the automatic analysis of cardiac M-Mode views.

2. Discussion of Related Art

In recent years echocardiography has become the most commonly used tool in diagnosis of heart disease. A standard 2D mode shows a planar slice of the heart across a scanning sector. By capturing multiple 2D frames in a video, the heart motion and function can be observed. Its ability to provide continuous view of both structure and motion, to take measurements and to verify functionality using blood and tissue Doppler are ever expanding and becoming more accurate. Yet, the outcome of these tests greatly depends on the sonographer skills, in particular depending on the accurate manual positioning of the sensor and of manually positioned calipers, rulers and markers over the captured images. Ultrasound images are, in general, low quality images. Because of the ultrasound imaging limitations, they have low resolution and suffer from very fuzzy edges, high noise and shadows. Their interpretation requires special training and rich experience, as defined in the "ACC/AHA Clinical Competence Statement on Echocardiography", 2002. For example, the minimum recommended training for a cardiologist is 6 months, performing at least 150 tests and interpreting another 300 tests.

Many of the required measurements are taken in M-mode—a spatio-temporal representation of the tissue motion along one scanning line of the ultrasound device through the heart. These measurements include estimations of ventricle volume, ejection fraction, tissue thickness, wall motion, valve timing and more. A typical echocardiogram test includes several 2D and M-Mode captures of different viewpoints, according to the "ACC/AHA/ASE 2003 Guideline Update for the Clinical Application of Echocardiography" and takes about 15-20 minutes.

The direct way of capturing and using an M-Mode of the heart is illustrated in FIG. 1 and FIG. 2. First, a 2D mode (see FIG. 1) is used to locate the chamber, reposition the sensor to see a cross section through the chamber and position a cursor (pointed to with an arrow) to pass through the chamber in a direction perpendicular to the walls. Then the scan mode and display mode are switched to M-Mode (FIG. 2). In this mode, the vertical axis corresponds to the z-axis, or depth from the sensor along the cursor line in the 2D mode. The horizontal axis corresponds to time. In this example, roughly two heart cycles are shown. The sonographer records several heart cycles, then freezes the view. The sonographer then places calipers (two vertical dotted lines 202, 204) and takes note of the measurements (from table 206). In this example the sonographer places two calipers, one at the end of diastolic period and the second at the end of systolic period. These calipers measure the short-axis diameter of the left chamber. The caliper-based measurements are then displayed in table 206. This whole process takes place during the patient echocardiogram test.

Hence, Direct M-Mode images can only be taken along a radial cursor line, origin from the sensor focal point. The sonographer has to accurately position the sensor device in a heart-depending orientation, often in conflict with the optimal positioning of the sensor to capture a good cross-section 2D view while avoiding bones, reducing interference and undesired reflections.

Panoramic M-Mode (also known as Anatomic M-Mode) is a process in which one or more synthetic M-Mode images is created from a sequence of 2D (or 3D) mode images by sampling those images along desired line(s) of scan and stacking those as columns in new M-Mode images. Compared to direct M-Mode, Panoramic M-Mode has the advantage of being generated in any direction and location on a 2D image rather than restricted by the sensor location. Panoramic M-Mode, however, suffers from lower temporal resolution, or scanning frequency. Panoramic M-Mode has been found very useful for diagnosis of Ischemia (see e.g., the paper to Lee et al. entitled, "Using Synthetic M-mode Imaging to Measure Temporal Differences in Left Ventricular Contraction Patterns during Ischemia"), measuring LV wall motion, wall thickening and more. Recently, Philips™ introduced Anatomic M-Mode into its EnVisor™ ultrasound system: " . . . and Anatomical M-mode that makes it easier to keep the M-mode line perpendicular to the anatomy—even in abnormally shaped or positioned hearts—and allows accurate measurements of chambers, walls, and ejection fraction."

While M-Mode has existed for decades and Panoramic M-Mode has just made its start into medical devices, there has been very little work on automatic analysis of M-Mode images using computer vision techniques. Griffiths et al., in their paper entitled, "Computer assisted M-mode echocardiogram analysis," use computer display and a tablet to allow users place calipers and mark traces, take measurements and render graphs corresponding to the user's marks on the image. Griffiths et al., however, do not apply any computer vision techniques. Maplica et al., in their paper entitled, "A snake model for anatomic M-mode tracking in echocardiography, Image and Signal Processing and Analysis", use snakes to track the evolution of a single Doppler blob in a panoramic M-Mode. However, Maplica et al. only deal with Doppler images containing single color blob of interest, while regular M-Mode images show many tissue layers and are more complex to analyze.

In U.S. Pat. No. 5,515,856, Olstad et al. provide a method for the generation of anatomic M-Mode images from 2D echocardiogram sequences. These images can then be used by a physician to aid in diagnosis. Olstad et al., however, do not provide means to automatically analyze the M-Mode image.

Potter et al., in U.S. Patent Publication 2006/0034538 A1, provide a general framework to: display echocardiogram images, take various measurements such as caliper-based measurements, and allow the physician to select measurement results and compose a report. Potter et al. disclose user interface workflow, such as acquiring a mouse click and responding to it, but it does not provide any method for analyzing the images and automatically extracting any measurements.

In U.S. Pat. No. 6,514,207, Ebadollahi et al. provide a method and system for analyzing the complete video of an echocardiogram test, segmenting and recognizing different modes and views along the exam, analyzing the overlay ECG graph, and detecting R-wave, thus segmenting the video into individual heart cycles. Ebadollahi et al., however, only analyze 2D views and do not deal with M-Mode images.

In U.S. Pat. No. 6,708,055, Gelser provides a method for analyzing a single frame of epical four chambers view using standard image processing techniques. Gelser, however, does not deal with M-Mode images. A single 2D view captures only a single snapshot of the heart, does not contain any temporal information and therefore does not allow the computation of an ejection fraction, or any motion-dependent or time-dependent measures.

In U.S. Pat. No. 4,936,311, Oe teaches how to analyze ventricular function using the center-line method, in which the long axis of the chamber in a 2D view is manually marked, followed by the manually marking of the area of difference between systolic and diastolic chamber views. The chamber volume and ejection fraction can then be estimated from the marked lines and regions. The process described by Oe is a labor intensive process. Also, Oe does not provide any image processing or other automatic way to analyze echocardiograms.

Prior art exists on image improvement of echocardiograms, such as reducing speckle as per the teachings of U.S. Pat. No. 6,755,787, wherein these methods may be applied as preprocessing to enhance image quality before applying the algorithm disclosed by Applicant's invention. However none of these prior art techniques teaches how to analyze the image content. Also, none of the existing works consider echocardiogram M-Mode images for automatic indexing and finding similar cases. Further, none of them provides any means to compare two M-Mode images. Hence there is need to define an appropriate representation, a method to efficiently construct it, allow to automatically extract medically meaningful measurements and a similarity measure, which enable the indexing and search for similar cases and therefore assist in multimodal medical decision support. Whatever the precise merits, features, and advantages of the above cited references, none of them achieves or fulfills the purposes of the present invention.

SUMMARY OF THE INVENTION

Automated analysis of M-Mode images are provided based on the separation of M-Mode images into tissue layers and motion curves by simultaneously aligning all layers and extracting the motion curves from the alignment. Also provided is the ability to search for similar M-Modes using a representation comprised of tissue layers and motion curves and a similarity measure thereof.

The present invention provides for a method comprising the steps of: receiving digital pixel data corresponding to one or more M-Mode images depicting at least a portion of an anatomical part; selecting a plurality of columns in the digital pixel data associated with a plurality of sample times; generating an alignment map by aligning the plurality of columns such that corresponding tissue layers match; constructing one or more motion curves using the alignment map, wherein the motion curves represent a motion pattern in the digital pixel data corresponding to the M-Mode images, the motion pattern separated from tissue layers identified in the alignment map; and outputting the one or more motion curves.

The present invention also provides for a method for comparing M-Mode images comprising of: receiving a plural of M-Mode images; for each image, computing at least one of tissue layers representation and motion curves representation; comparing the motion curves and or the tissue layers of at least two images; determining a similarity value between the at least two image pair; and outputting the similarity value.

The present invention also provides for an article of manufacture having computer usable medium storing computer readable program code implementing a computer-based method, wherein the medium comprises: computer readable program code aiding in receiving digital pixel data corresponding to one or more M-Mode images depicting at least a portion of an anatomical part; computer readable program code selecting a plurality of columns in the digital pixel data; computer readable program code generating an alignment map by aligning the plurality of columns such that corresponding tissue layers match; computer readable program code constructing one or more motion curves using the alignment map, wherein the motion curves represent a motion pattern in the digital pixel data corresponding to the M-Mode images, the motion pattern separated from tissue layers identified in the alignment map; and computer readable program code outputting the one or more motion curves.

DESCRIPTION OF THE PREFERRED EMBODIMENTS

Figure 1:
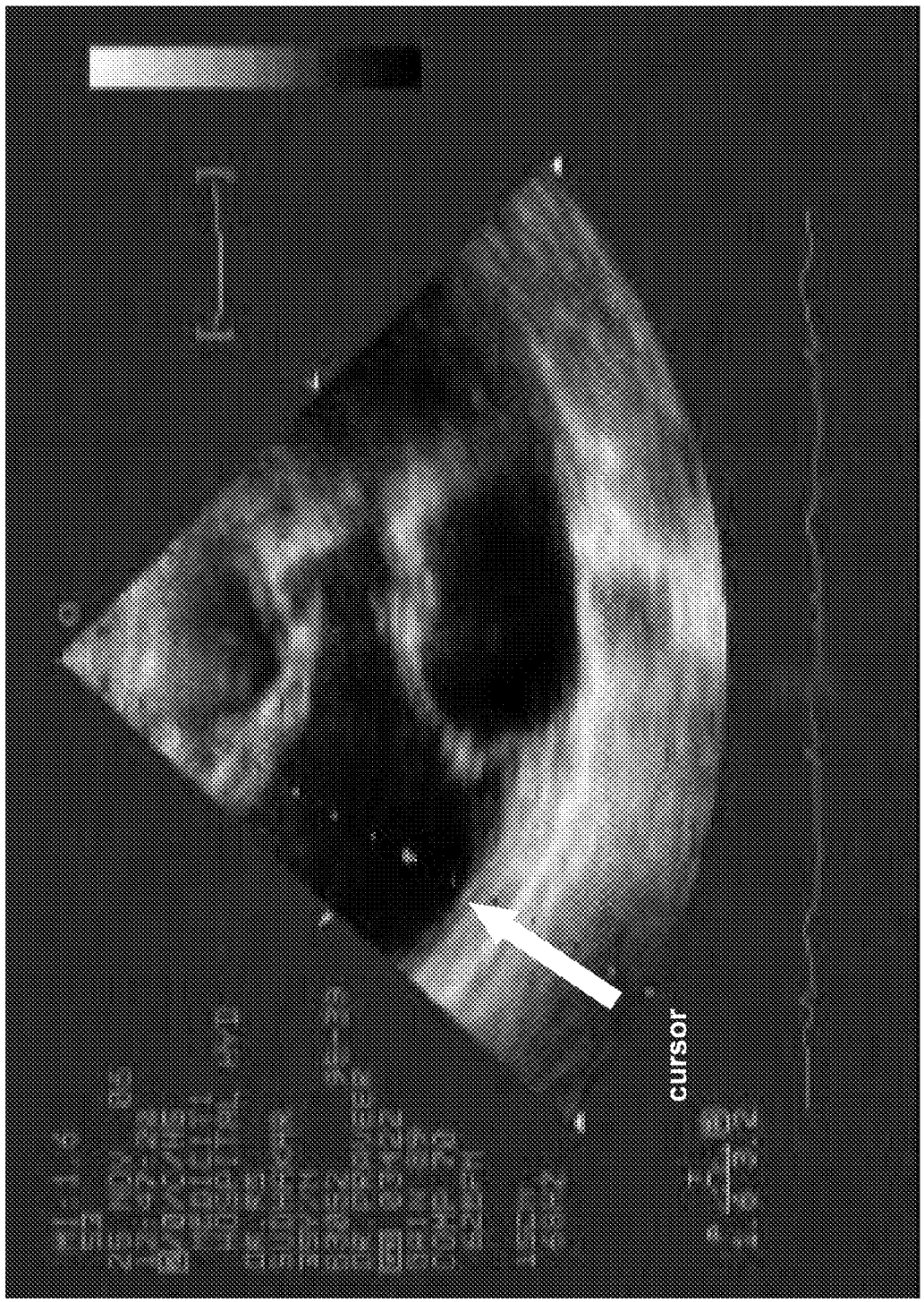
FIG. 1 and FIG. 2 illustrate the direct way of capturing and using an M-Mode of the heart.
Figure 2:
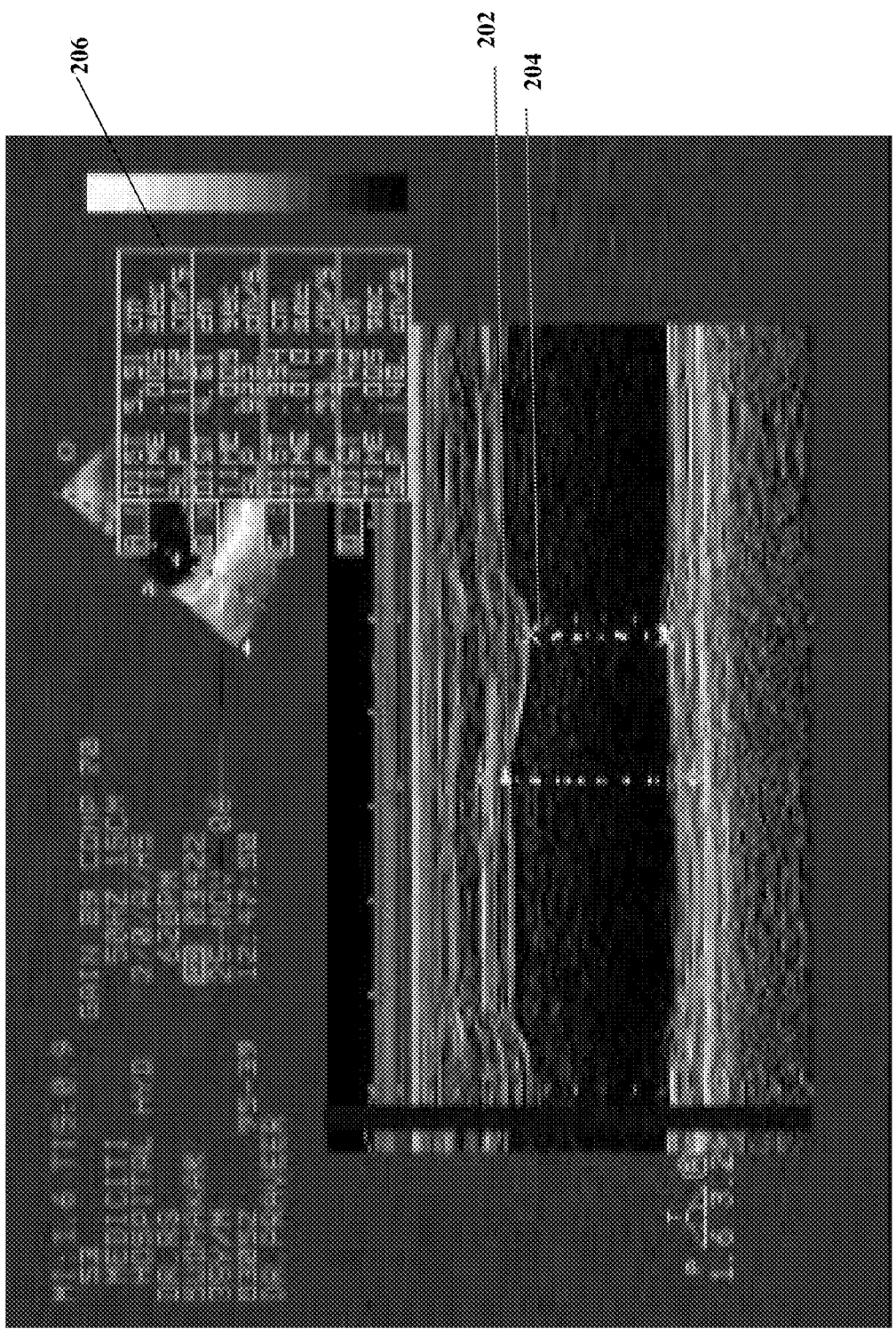

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

The present invention provides for the automatic analysis of echocardiograms M-Mode views, wherein the present invention's method creates an informative and efficient representation of echocardiogram M-Mode images by decoupling tissue layers and motion curves, whereby such decoupling allows: (a) the extraction of various physical and functional characteristics of the heart, such as ejection fraction and left ventricle (LV) wall thickness; (b) the comparison of two echocardiograms (hereon noted echoes), taken from the same patient at different times or from two different patients, (c) the indexing and searching for similar cases in large electronic medical records (EMR) containing patient's echoes.

Comparing medical records, including various test data, has been identified as a promising direction in multimodal medical decision support. Further, it has potential in increasing automation of echocardiogram analysis and reducing human errors.

M-Mode views can be generated in different ways, directly captured by the echocardiogram device or as a Panoramic M-Mode.

The present invention provides for the analysis of these views, wherein a new approach is disclosed for M-Mode analysis using dynamic time wrapping across tissue layers for continuous spatial alignment of all layers during heart motion, and a new low dimensional image representation is disclosed wherein the motion and tissue representations are decoupled.

Figure 3:
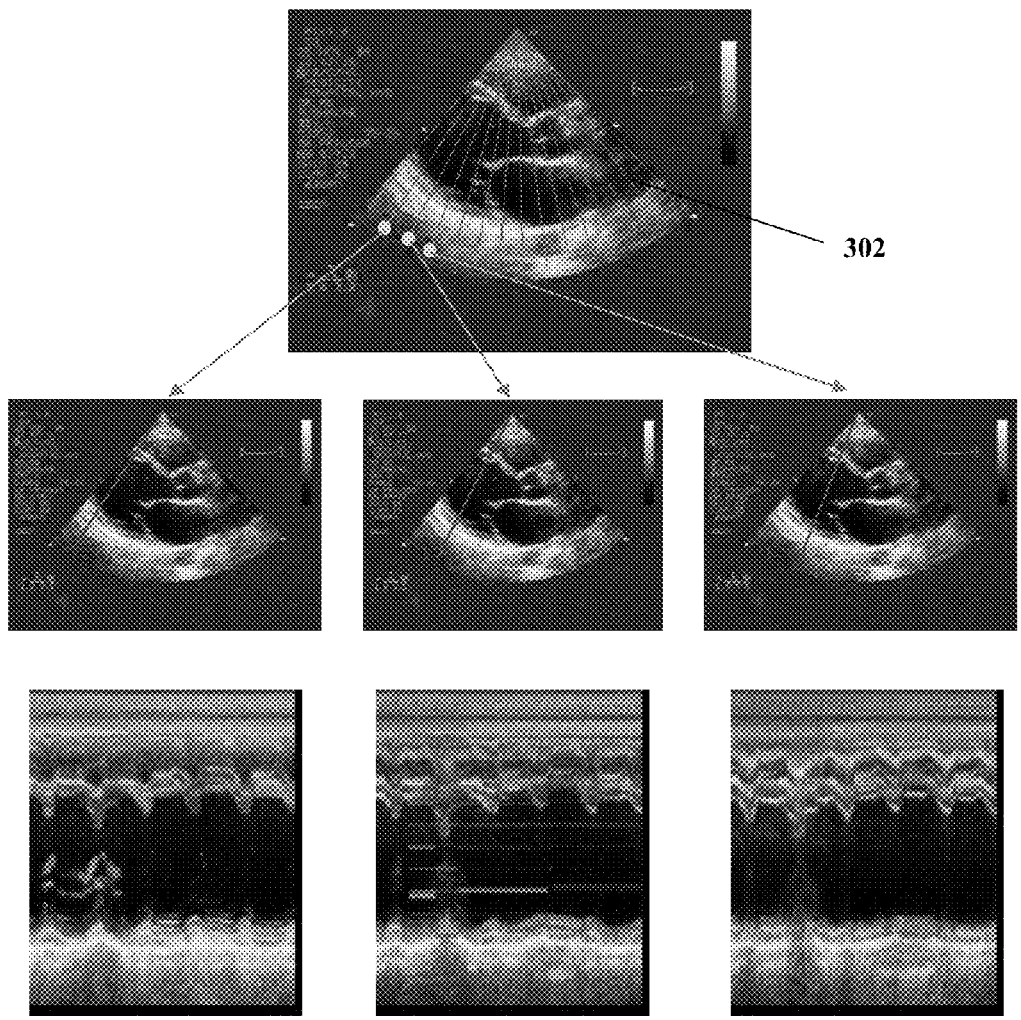
FIG. 3 illustrates the generation of a panoramic M-Mode from multiple 2D frames.

FIG. 3 illustrates the generation of a panoramic M-Mode from multiple 2D frames. Each line, such as line 302, corresponds to the principle axis of one synthetic M-Mode image. Three examples are shown below, with their corresponding principle axes. Each of the synthetic M-Mode frames is created by sampling a multiple of 2D frames along the selected principle axis (as described above).

The present invention's algorithm works as follows: (a) take an M-Mode image, extract the echo region of the image (Region of Interest—ROI); (b) select a first reference column of pixels; (c) for each column i=1 ... n: compute rdtw(c_i, c_ref) (rdtw stands for Relaxed Dynamic Time Warping), and update c_ref as a linear combination of c_ref and warp(c_i).

According to one embodiment of the present invention, first the echo ROI is found, wherein the ROI includes the echo region and excludes the textual and graphics found around it. When extracted from an M-Mode frame that was captured by an echocardiogram machine, the ROI is extracted as a large rectangle area having a distinct gray levels histogram compared to the background. An initial rectangle is placed over the image and the gray levels histogram is computed for both the inside and the outside of the rectangle area. Next, the difference between these histograms is computed. Then, small changes are introduced to the rectangle location and/or size, and the histograms are recomputed. The process stops when no improvement to the distance between the two histograms is observed.

Figure 4:
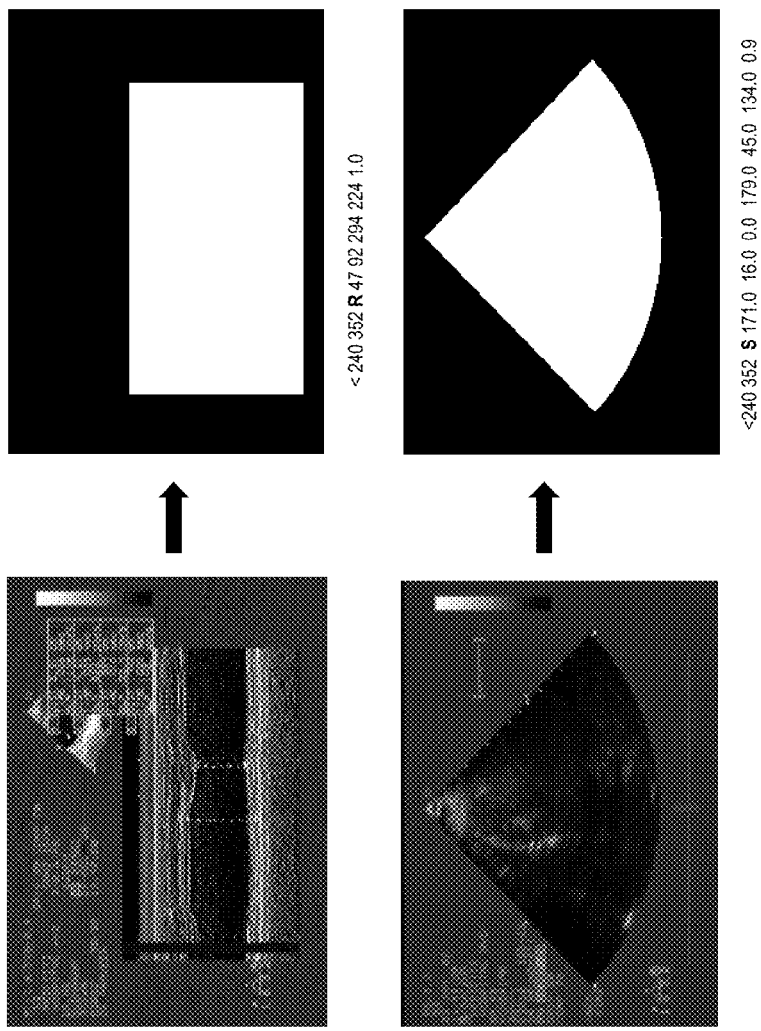
FIG. 4 illustrates the extraction of the echo region from an echocardiogram video frame.

FIG. 4 illustrates the extraction of the echo region from an echocardiogram video frame. All but the echo video content is removed by a mask with shape and size corresponding to the shape and size of the echo region (Region of Interest, denoted ROI). The mask can be computed automatically using image processing techniques or it can be marked manually. A mask can be efficiently represented by its coordinates in pixels, as exemplified by the set of numbers below the mask image. For the rectangle ROI, the mask descriptor includes the frame dimensions, coordinates of the corners and the aspect-ratio of the pixels. For the sector shape ROI, the frame dimensions, center coordinates of the circle, small and large radius, begin and end angles and the aspect ratio are stored.

Other methods could be used to find the ROI, such as the Hough transform, as taught in the paper to Duda et al., "Use of the Hough Transformation to Detect Lines and Curves in Pictures."

In the case of a Panoramic M-Mode, the panoramic generation process creates an echo image which contains just the M-Mode echo ROI. Therefore, no ROI detection is needed.

Figure 5:
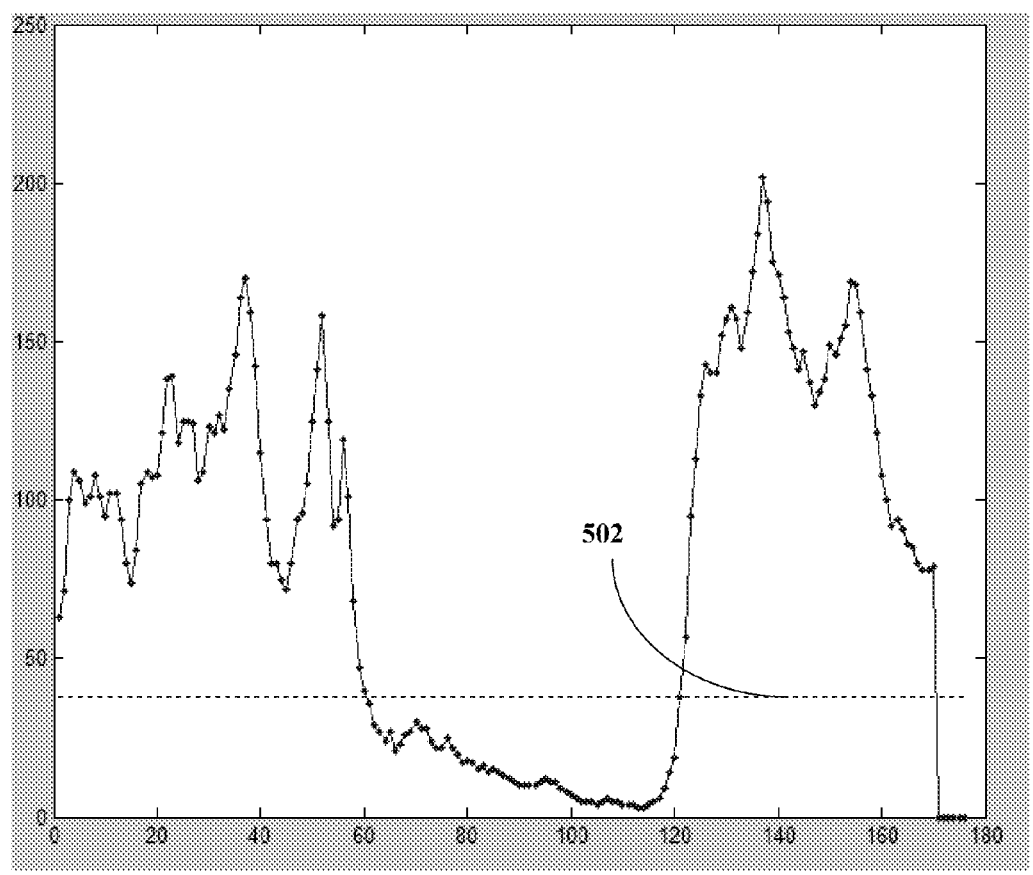
FIG. 5 illustrates a graph of the median gray levels of the pixels along the various pixel columns.

Next, a reference column of pixels is selected from the echo. Each column of pixels in the echo is associated with a point in time—the time when this sample was taken. Hence the horizontal axis of an M-Mode echo is a time axis, measured in seconds. The vertical axis of the M-Mode image represents a line of scan in 3D going through the heart. Hence the measuring units on the vertical axis are centimeters. A reference column is selected by first computing the median gray level in each row of pixels, thereby creating a median column as a reference column. The median is shown in FIG. 5 as line 502, where the median gray levels of the pixels along the column are represented as a graph. The horizontal axis represents pixel location along the column (row number, or y coordinate of the pixel in the image). The vertical axis represents the median gray level along that row of pixels in the image. The zero value represents black and the 255 value represents white. The large valley roughly in the middle of the graph of FIG. 5 corresponds to pixels in the black area, roughly in the middle of the echo, generally corresponding to the inner of the ventricle, filled with fluid (i.e., blood). Other ways to select a reference column include the selection of a column at a particular time of the heart cycle, such as the end of systolic period or end of diastolic period.

Then, each of the echo columns is compared with the median column. The column which is found to be the closest to the median is selected as the reference column. This column is marked in FIG. 6 by line at 602 the bottom of the figure. Column alignment is then computed for the remaining columns. The process starts from the reference column and progresses to left and right columns. The algorithm is provided below:

Alignment Algorithm, Using Relaxed Time Warping Algorithm:

```
rHistory = r = rRef;
for i=1:n
    t=M(:,cols(i))';
    [Dist,D,ki,wi]=dtwrlx(r,t,2.0);
    wrap_t(wi(:,1))=wi(:,2);
    rHistory=alpha*rHistory+(1-
alpha)*t(wrap_t(wi(:,1)));
    r = alphaRef*rRef+(1-alphaRef)*rHistory;
end
```

Figure 6:
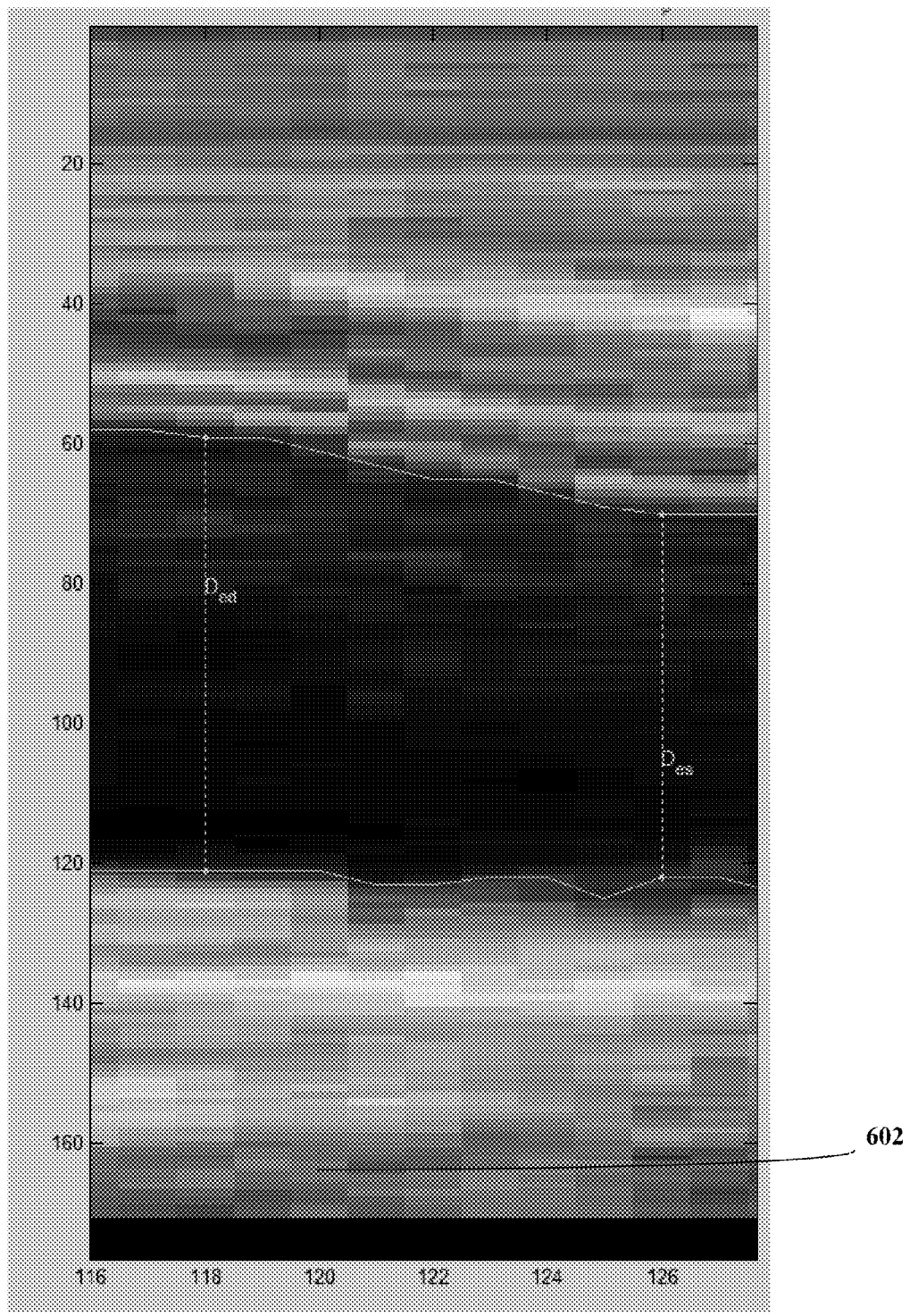
FIG. 6 illustrates a small section of an M-Mode image making individual columns of pixels visible.
Figure 7:
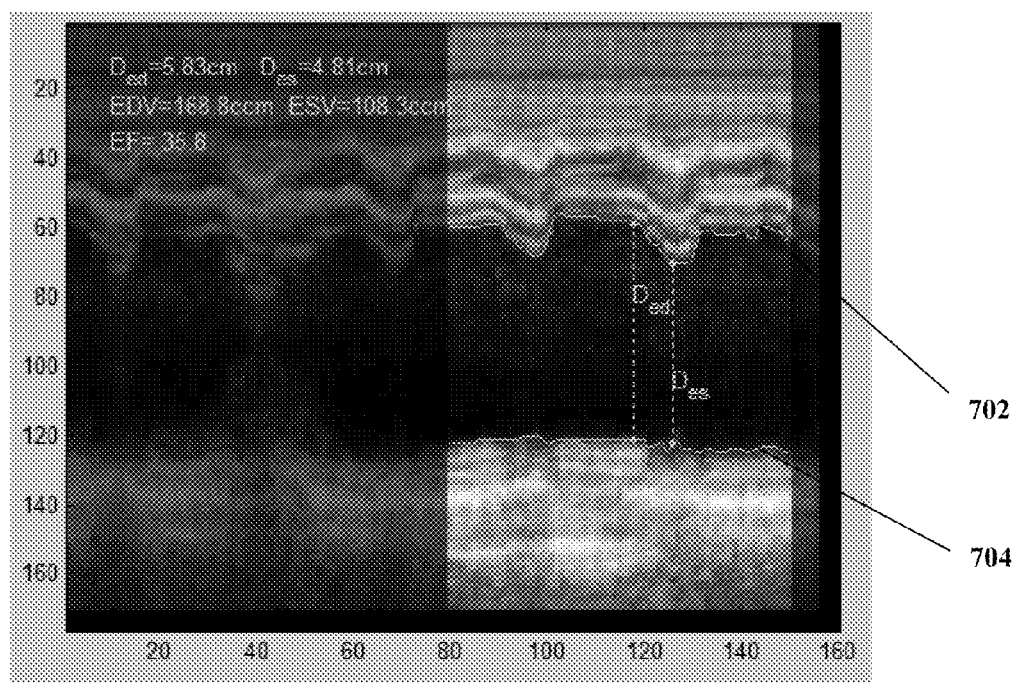
FIG. 7 illustrates an example of an M-Mode ROI region, superimposed with processing output of the ventricle walls.

At each iteration, a column t is aligned with a reference column r and the resulted mapping between the two is written to an array wrap_t. Further, rhistory is computed to represent the cumulative history of traces through aligned columns. Then, r is updated to be a linear combination of the reference column rRef and the cumulative history, rHistory. There are other ways to compute the alignment, directly to rRef or with other columns. The result would be either a mapping from each column to the reference column, or to the adjacent column. This mapping allows tracing and reconstructing paths along tissue layers along time. Example for tracing is shown in FIG. 7 and a zoom is shown in FIG. 6, where individual columns of pixels are visible.

The alignment of two columns is performed using a Dynamic Time Warping algorithm. The DTW algorithm is used in the alignment of time-varying signals. An example of a known Dynamic Time Warping algorithm is provided below:

```
int DTWDistance(char s[1..n], char t[1..m], int
d[1..n,1..m]) {
    declare int DTW[0..n,0..m]
    declare int i, j, cost
    for i := 1 to m
        DTW[0,i] := infinity
    for i := 1 to n
        DTW[i,0] := infinity
    DTW[0,0] := 0
```

-continued

```
    for i := 1 to n
        for j := 1 to m
            cost:= d[s[i],t[j]]
            DTW[i,j] := cost + minimum(DTW[i−1,j ], // insertion
                                      DTW[i ,j−1], // deletion
                                      DTW[i−1,j−1]) // match
        return DTW[n,m]
    }
```

In general, it computes the alignment between a signal s(t) and a signal r(t) by finding the best time-warping function d that minimizes |s(d(t))−r(t)|. In other words, it finds a time mapping that modifies s(t) and maps it onto r(t).

Here, a variation of DTW is used, denoted as Relaxed DTW, as shown below:

Relaxed Dynamic Time Warping Algorithm

```
    D=zeros(size(d));
    upCost=zeros(size(d)); % accumulated cost of next
    consequent up step
    rtCost=zeros(size(d)); % accumulated cost of next
    consequent right step
    D(1,1)=d(1,1);
    UpCostFactor = 1000;
    RtCostFactor = 1000;
    UpCostExp = 1.5;
    RtCostExp = 1.5;
    for n=2:N
        D(n,1)=d(n,1)+D(n−1,1);
    end
    for m=2:M
        D(1,m)=d(1,m)+D(1,m−1);
    end
    for n=2:N
        for m=2:M
            Drt=D(n,m−1)+rtCost(n,m−1);
            Dup=D(n−1,m)+upCost(n−1,m);
            Dur=D(n−1,m−1);
            if (Dur<=Drt)
                if (Dur<=Dup) % Dur
                    D(n,m)=d(n,m)+Dur;
                else % Dup
                    D(n,m)=d(n,m)+Dup;
                    upCost(n,m)=UpCostExp*upCost(n−
    1,m)+UpCostFactor;
                end
            else
                if (Drt<Dup) % Drt
                    D(n,m)=d(n,m)+Drt;
                    rtCost(n,m)=RtCostExp*rtCost(n,m−
    1)+RtCostFactor;
                else % Dup
                    D(n,m)=d(n,m)+Dup;
                    upCost(n,m)=UpCostExp*upCost(n−
    1,m)+UpCostFactor;
                end
            end
        end
    end
```

This algorithm extends DTW and differs from it by penalizing mappings with large skew. While this variant has some advantages over DTW for echo alignment, other time-warping algorithms and criteria may be used. For example, the viscosity and elasticity of tissues may be taken into account in the DTW computation. This invention is not limited to a specific method for time warping. A comparison between various DTW algorithms can be found in the paper to Myers et al. titled "A comparative study of several dynamic time-warping algorithms for connected word recognition".

Figure 8:
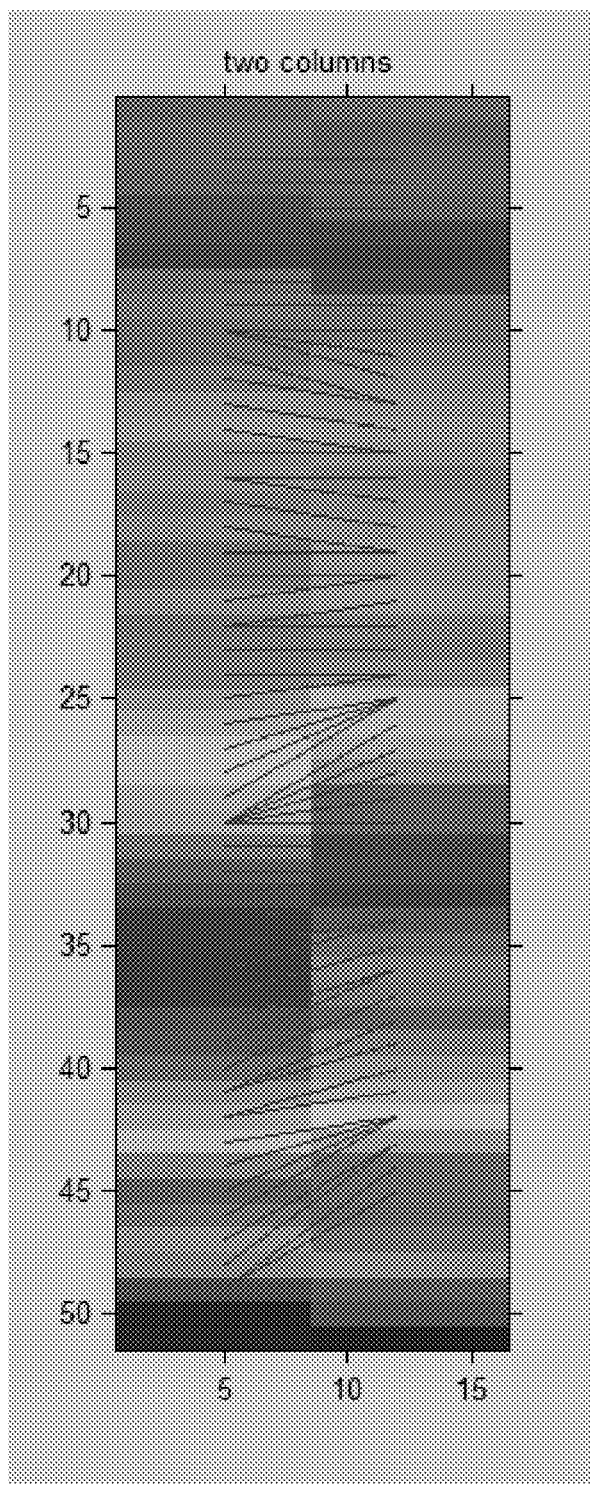
FIG. 8 illustrates an example of time-warping between two columns of pixels.

An example for the alignment between two columns of M-Mode pixels is shown in FIG. 8. Here, an enlargement of one portion of just two columns of pixels is shown. Long gray level boxes represent the pixels in each column. Lines are connecting pixels aligned by the algorithm. The line connecting pixel i in the left column with pixel j in the right column is stored in the alignment vector wi(i,1) and wi(i,2), respectively. By following each such line to the next column and then continuing with the mapping from that column to the consequent column and so on, we are able to construct paths along the M-Mode image, following a layer of tissue. For example, see curves 702 and 704 in FIG. 7 and in enlarged portion shown in FIG. 6. Those lines follow the ventricle wall boundary. $D_{ed}$ and $D_{es}$ represent end-diastolic dimension and end-systolic dimension, respectively.

Figure 9:
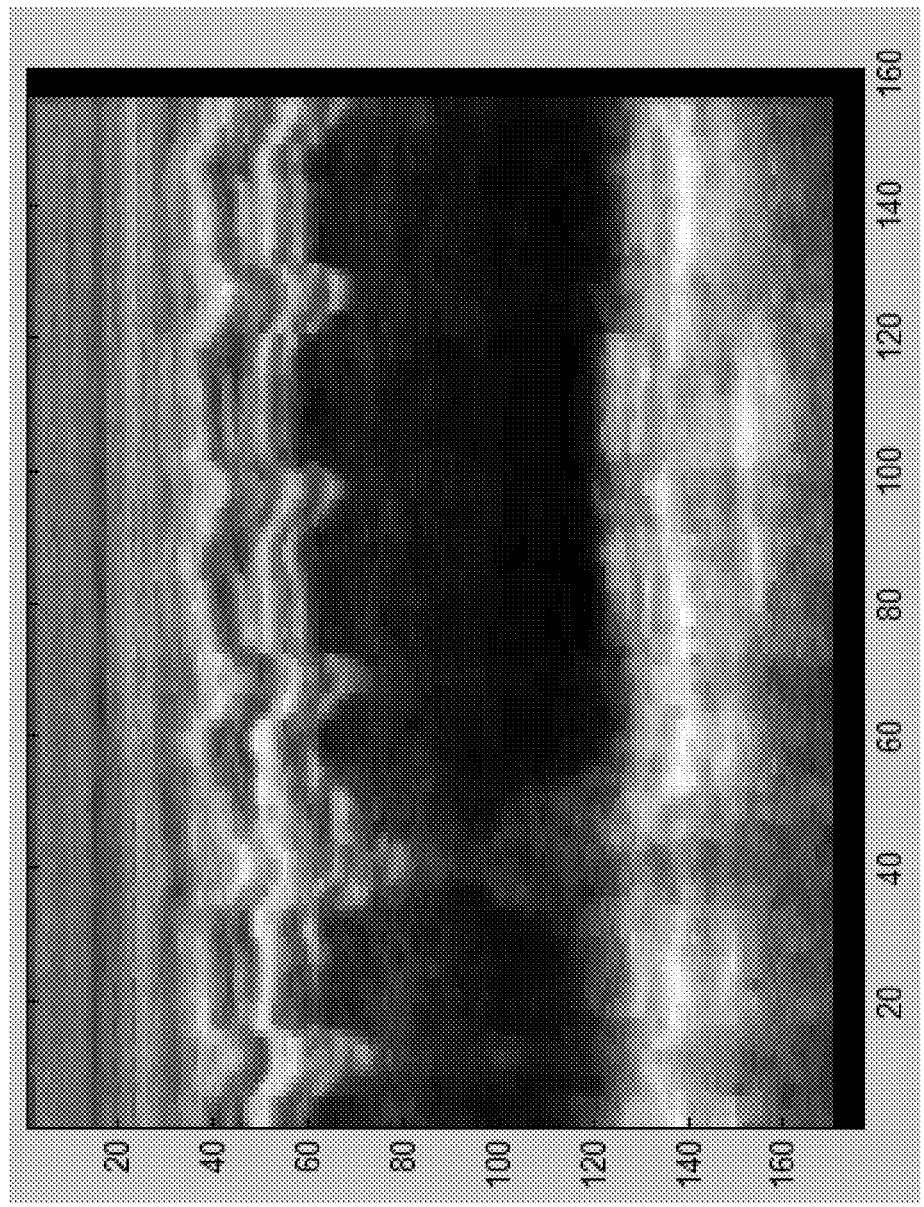
FIG. 9 illustrates of an M-original image.

FIG. 9 illustrates the original M-Mode echo region, generated as a Panoramic M-Mode, and FIG. 7 illustrates the resulted image after computing the wrapping of all columns and superimposing the detected motion curves on the image. As can be observed, the motion has been removed, and only the tissue layers are present. Another complementary part of the output is the warping mapping. It only describes the motion of each pixel, in the form of a curve going from left to right and following the motion of that tissue layer (see 702 and 704 of FIG. 7).

Figure 10:
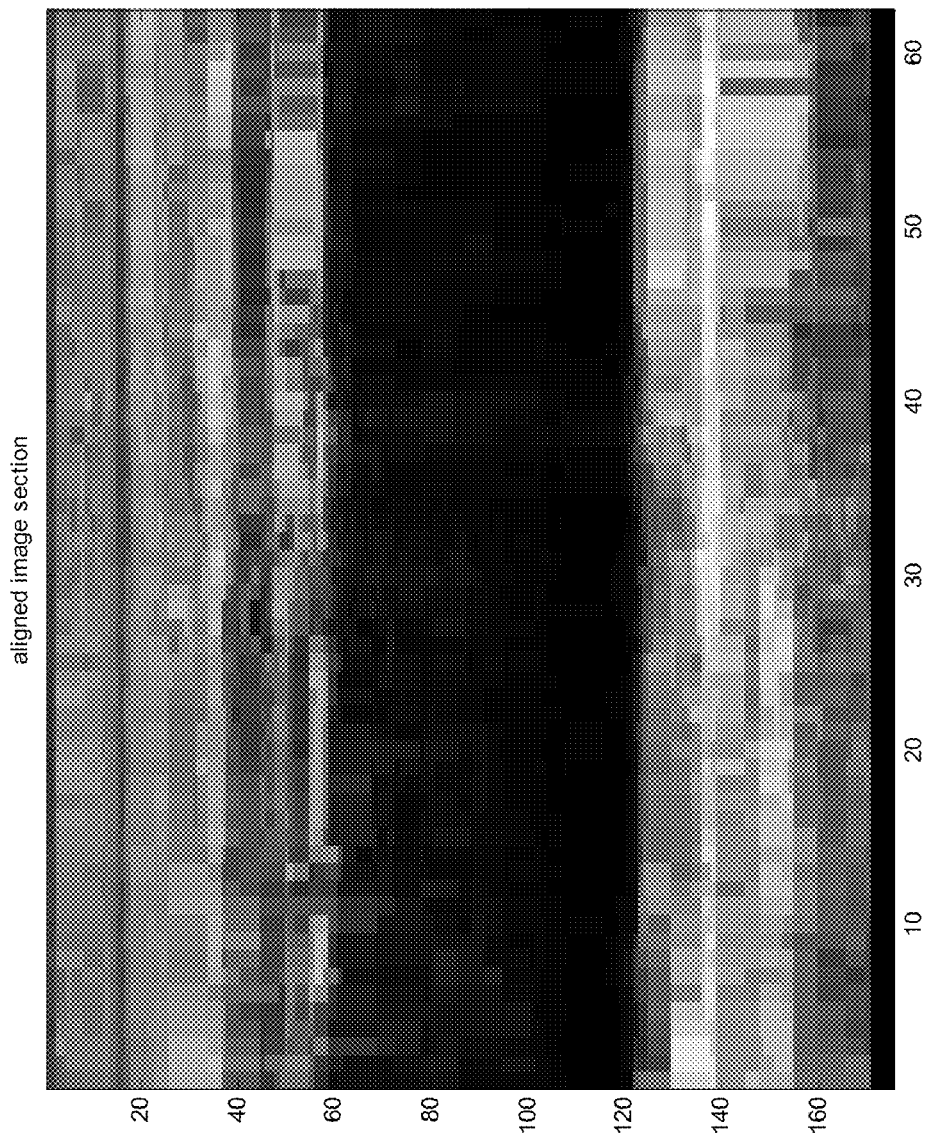
FIG. 10 illustrates an example of an M-Mode image after alignment of tissue layers along time and removal of motion (vertical component).

FIG. 10 illustrates an example of an M-Mode image after alignment of tissue layers along time and removal of motion (vertical component). Layers appear to show horizontal regions. Edges between layers can be detected by image processing techniques, taking advantage of the horizontal image structure, e.g., by projecting the gray levels on the vertical axis and computing statistical model for each tissue layer. For example, one could use a Gaussian Mixture Model (GMM) to model the tissue layers.

Figure 11:
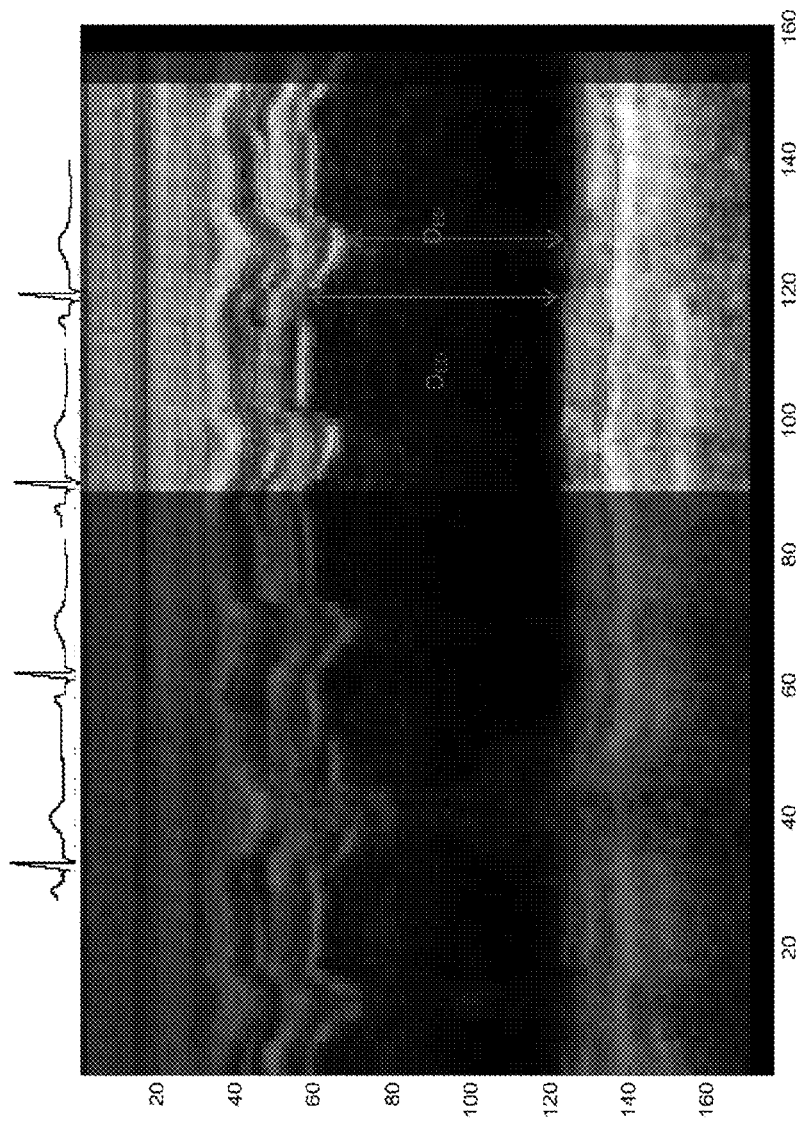
FIG. 11 shows a panoramic M-Mode image, where part of the image, corresponding roughly to two heart cycles, has been processed by the proposed method.

FIG. 11 shows a panoramic M-Mode image, where part of the image, corresponding roughly to two heart cycles, has been processed by the proposed method. The processed part is marked by a brighter window. The processing results are illustrated by superimposing the image with blue curves, corresponding to the motion of several tissue layers. $D_{ed}$ and $D_{es}$ represent end-diastolic dimension and end-systolic dimension, respectively.

The present invention, therefore, provides for a novel representation of M-Mode images, wherein it can be used to characterize the M-Mode image by separately representing the tissue composition and the motion pattern. Motion curves are in general smooth curves and can be represented, for example, as splines, using a small number of coefficients. Tissue layers can be represented by a single column such as the mean value in each line.

The present invention provides for a method for analyzing cardiac M-Mode images comprising the steps of: (a) receiving digital pixel data corresponding to one or more M-Mode images depicting at least a portion of an anatomical part; (b) selecting a plurality of columns in the pixel data; (c) generating an alignment map by aligning the plurality of columns such that corresponding tissue layers match; and (d) constructing one or more motion curves using the alignment map, wherein the motion curves represent a motion pattern in the digital pixel data corresponding to the M-Mode images, the motion pattern separated from tissue layers identified in the alignment map.

In one embodiment, the alignment map is further used to wrap a plurality of the aligned columns and generate a synthetic image in which tissues are aligned and show no (vertical) motion. In an extension to this embodiment, the generated synthetic image is used to generate a tissue layers representation which is motion independent.

In one embodiment, alignment is made using a dynamic time warping technique, wherein the vertical (column) axis serves as the "time" for warping computation.

The present invention also provides for a method for comparing M-Mode images comprising the steps of: receiving digital pixel data corresponding to a plural of M-Mode images, and for each image, computing at least one of tissue layers representation and motion curves representation, and comparing the motion curves and/or the tissue layers of at least two images and determining a similarity value between the image pair. The similarity value depends on the comparison method used, i.e., depends on the Euclidean distance or dynamic time warping (DTW) distance, and can be normalized to be in the range 0.0 to 1.0.

In one embodiment, the above-described method is applied to find the most similar ones (nearest neighbors) to a given M-Mode image within a collection of M-Mode images.

In one embodiment, the above described method is applied to find the Ejection Fraction (EF) of the left ventricle as follows:

$$EF(\%) = \frac{V_{ed} - V_{es}}{V_{ed}} \times 100$$

where:

$$V_{ed} = \frac{7 D_{ed}^3}{2.4 + D_{ed}} \text{ and } V_{es} = \frac{7 D_{es}^3}{2.4 + D_{es}},$$

and $D_{ed}$ and $D_{es}$ represent end-diastolic dimension and end-systolic dimension, respectively.

The Teichholtz formula is applied to estimate the volume of the left ventricle from its diameter. The diameter is measured between two curves as illustrated in FIG. 7, one positioned at the end of the systolic period and the other is positioned at the end of the diastolic period.

Although the present invention has been described with respect to two-dimensional data, it should be noted that the teachings of the present invention can be extended to higher dimensional data, and such extensions are within the scope of the present invention. Also, although cardiac data has been used extensively in the examples of the specification, it should be noted that the present invention's teachings may be applied to ultrasound images of other parts of the body when tested under motion, such as lungs. The type of ultrasound image should not be used to limit the scope of the present invention. Further, although ultrasound images have been disclosed in the specification, it should be noted that the present invention's teachings may be applied to other imaging modalities than ultrasound (thus its main advantage is in dealing with noisy data).

Additionally, the present invention provides for an article of manufacture comprising computer readable program code contained within implementing one or more modules to separate M-Mode images into tissue layers and motion curves by simultaneously aligning all layers and extracting the motion curves from the alignment and one or modules to search for similar M-Modes using a representation comprised of tissue layers and motion curves and a similarity measure thereof. Furthermore, the present invention includes a computer program code-based product, which is a storage medium having program code stored therein which can be used to instruct a computer to perform any of the methods associated with the present invention. The computer storage medium includes any of, but is not limited to, the following: CD-ROM, DVD, magnetic tape, optical disc, hard drive, floppy disk, ferroelectric memory, flash memory, ferromagnetic memory, optical storage, charge coupled devices, magnetic or optical cards, smart cards, EEPROM, EPROM, RAM, ROM, DRAM, SRAM, SDRAM, or any other appropriate static or dynamic memory or data storage devices.

Figure 12:
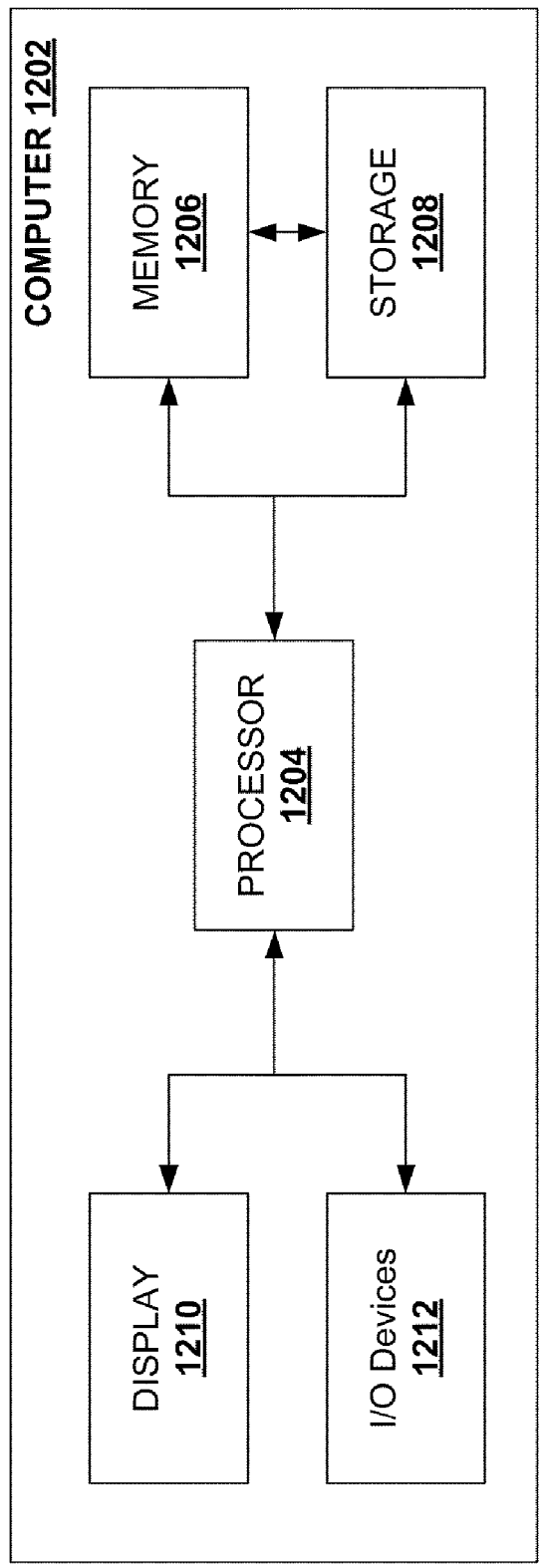
FIG. 12 illustrates an exemplary computer-based system used to implement the present invention's method to analyze and compare cardiac M-Mode images.

The present invention provides a computer-based system 1202, as shown in FIG. 12, to implement a method to analyze and compare cardiac M-Mode images. The computer system shown in FIG. 22 comprises processor 1204, memory 1206, storage 1208, display 1210, and input/output devices 1212. Storage 1208 stores computer readable program code implementing one or more modules for analyzing and comparing cardiac M-Mode images.

Stored within storage 1208 are computer readable program code implementing a computer-based method, wherein computer readable program code: aids in receiving digital pixel data corresponding to one or more M-Mode images depicting at least a portion of an anatomical part; selects a plurality of columns in the digital pixel data; generates an alignment map by aligning the plurality of columns such that corresponding tissue layers match; constructs one or more motion curves using the alignment map, wherein the motion curves represent a motion pattern in the digital pixel data corresponding to the M-Mode images, the motion pattern separated from tissue layers identified in the alignment map; and outputs the motion curves.

CONCLUSION

A system and method has been shown in the above embodiments to automatically analyze and/or compare cardiac M-Mode views. While various preferred embodiments have been shown and described, it will be understood that there is no intent to limit the invention by such disclosure, but rather, it is intended to cover all modifications falling within the spirit and scope of the invention, as defined in the appended claims.

The invention claimed is:
1. A method comprising:
receiving digital pixel data corresponding to one or more M-Mode images depicting at least a portion of an anatomical part;
selecting a plurality of columns in said digital pixel data associated with a plurality of sample times;
generating an alignment map by aligning said plurality of columns such that corresponding tissue layers match;
constructing one or more motion curves using said alignment map, wherein said motion curves represent a motion pattern in said digital pixel data corresponding to said M-Mode images, said motion pattern separated from tissue layers identified in said alignment map;
outputting said one or more motion curves;
wrapping, based on the alignment map, a plurality of aligned columns and generating a synthetic image in which tissues are aligned and show no vertical motion;
generating, based on the synthetic image, a tissue layers representation that is motion independent; and
computing the generated tissue layers representation as a vector of scalars, wherein each vector correspond to a median or an average gray level along row of pixels in the synthetic image.
2. The method of claim 1, wherein the method further comprises outputting the generated tissue layers representation as a curve representing a median or an average gray level along row of pixels in the synthetic image.

3. The method of claim 1 wherein the method further comprises aligning a plurality of vertical columns via a dynamic time warping technique.

4. The method of claim 1, wherein the method further comprises selecting a plurality of motion curves corresponding to at least one tissue layer, and computing a motion magnitude motion between at least two time points on said plurality of motion curves.

5. The method of claim 1, wherein the method further comprises selecting a plurality of motion curves corresponding to at least one tissue layer, and computing a distance between at least two curves at least at one point in time.

6. A method comprising:
receiving digital pixel data corresponding to one or more M-Mode images depicting at least a portion of an anatomical part;
selecting a plurality of columns in said digital pixel data associated with a plurality of sample times;
generating an alignment map by aligning said plurality of columns such that corresponding tissue layers match;
constructing one or more motion curves using said alignment map, wherein said motion curves represent a motion pattern in said digital pixel data corresponding to said M-Mode images, said motion pattern separated from tissue layers identified in said alignment map;
outputting said one or more motion curves;
wherein said anatomical part is the human heart and the method comprises calculating an end-diastolic dimension, $D_{ed}$, and an end-systolic dimension, $D_{es}$ from the constructed motion curves, and calculating and outputting an Ejection Fraction (EF) of the left ventricle of the human heart as follows:

$$EF(\%) = \frac{V_{ed} - V_{es}}{V_{ed}} \times 100$$

where:

$$V_{ed} = \frac{7D_{ed}^3}{2.4 + D_{ed}} \text{ and } V_{es} = \frac{7D_{es}^3}{2.4 + D_{es}}.$$

7. An article of manufacture having non-transitory computer usable medium storing computer readable program code implementing a computer-based method, said medium comprising:
computer readable program code aiding in receiving digital pixel data corresponding to one or more M-Mode images depicting at least a portion of an anatomical part;
computer readable program code selecting a plurality of columns in said digital pixel data;
computer readable program code generating an alignment map by aligning said plurality of columns such that corresponding tissue layers match;
computer readable program code constructing one or more motion curves using said alignment map, wherein said motion curves represent a motion pattern in said digital pixel data corresponding to said M-Mode images, said motion pattern separated from tissue layers identified in said alignment map;
computer readable program code outputting said one or more motion curves;
computer readable program code wrapping, based on the alignment map, a plurality of aligned columns and generating a synthetic image in which tissues are aligned and show no vertical motion;
computer readable program code generating, based on the synthetic image, a tissue layers representation which is motion independent; and
computer readable program code computing the generated tissue layers representation as a vector of scalars, wherein each vector correspond to a median or an average gray level along row of pixels in the aligned synthetic image.

8. The article of manufacture of claim 7, wherein the medium further comprises computer readable program code outputting the generated tissue layers representation as a curve representing a median or an average gray level along row of pixels in the aligned synthetic image.

9. The article of manufacture of claim 7, wherein the medium further comprises computer readable program code aligning a plurality of vertical columns via a dynamic time warping technique.

10. The article of manufacture of claim 7, wherein said anatomical part is the human heart and the medium further comprises computer readable program code calculating an end-diastolic dimension, $D_{ed}$, and an end-systolic dimension, $D_{es}$ from the constructed motion curves, and computer readable program code calculating and outputting an Ejection Fraction (EF) of the left ventricle of the human heart is further calculated as follows:

$$EF(\%) = \frac{V_{ed} - V_{es}}{V_{ed}} \times 100$$

where:

$$V_{ed} = \frac{7D_{ed}^3}{2.4 + D_{ed}} \text{ and } V_{es} = \frac{7D_{es}^3}{2.4 + D_{es}}.$$

* * * * *